United States Patent
Bi

(10) Patent No.: US 10,263,044 B2
(45) Date of Patent: Apr. 16, 2019

(54) TANDEM ORGANIC LIGHT-EMITTING DIODE, ARRAY SUBSTRATE AND DISPLAY DEVICE

(71) Applicant: BOE Technology Group Co., Ltd., Beijing (CN)

(72) Inventor: Wentao Bi, Beijing (CN)

(73) Assignee: BOE Technology Group Co., Ltd., Beijing (CN)

(*) Notice: Subject to any disclaimer, the term of this patent is extended or adjusted under 35 U.S.C. 154(b) by 218 days.

(21) Appl. No.: 15/323,152

(22) PCT Filed: Apr. 21, 2016

(86) PCT No.: PCT/CN2016/079885
§ 371 (c)(1),
(2) Date: Dec. 30, 2016

(87) PCT Pub. No.: WO2017/000635
PCT Pub. Date: Jan. 5, 2017

(65) Prior Publication Data
US 2017/0200770 A1  Jul. 13, 2017

(30) Foreign Application Priority Data

Jun. 29, 2015 (CN) .......................... 2015 1 0370268

(51) Int. Cl.
*C07C 9/22* (2006.01)
*C07C 15/38* (2006.01)
(Continued)

(52) U.S. Cl.
CPC ................ *H01L 27/32* (2013.01); *C07C 9/22* (2013.01); *C07C 15/38* (2013.01); *C07C 211/54* (2013.01);
(Continued)

(58) Field of Classification Search
CPC ......... C07C 15/38; C07C 211/54; C07C 9/22; C07D 209/58; C07D 235/20;
(Continued)

(56) References Cited

U.S. PATENT DOCUMENTS 7,494,722 B2*  2/2009  Liao ................... H01L 51/5278
                                                         257/E51.022
7,816,859 B2*  10/2010  Spindler ............... C09K 11/06
                                                         313/504
(Continued)

FOREIGN PATENT DOCUMENTS

CN          101447555 A       6/2009
CN          101515633 A       8/2009
(Continued)

OTHER PUBLICATIONS

Machine translation CN 103022366 A (publication date: Apr. 2013). (Year: 2013).*
(Continued)

*Primary Examiner* — Dawn L Garrett
(74) *Attorney, Agent, or Firm* — Banner & Witcoff, Ltd.

(57) ABSTRACT

A tandem organic light-emitting diode, an array substrate and a display device are provided. The tandem organic light-emitting diode includes an anode, a hole transport layer, a first light-emitting layer, a first charge generation layer, a second charge generation layer, a third charge generation layer, a fourth charge generation layer, a second light-emitting layer, an electron transport layer and a cathode which are sequentially laminated, wherein the first charge generation layer is an N-type bulk heterojunction, the second charge generation layer and the third charge generation layer are both PN junction type bulk heterojunctions, a proportion of the P-type organic material in the second charge generation layer is greater than that of the N-type organic material, a proportion of the P-type organic material
(Continued)

in the third charge generation layer is less than that of the N-type organic material, and the fourth charge generation layer is a P-type bulk heterojunction.

17 Claims, 1 Drawing Sheet

(51) Int. Cl.
| | |
|---|---|
| C07F 15/00 | (2006.01) |
| H01L 27/32 | (2006.01) |
| H01L 51/50 | (2006.01) |
| H01L 51/52 | (2006.01) |
| C07C 211/54 | (2006.01) |
| C07D 209/58 | (2006.01) |
| C07D 235/20 | (2006.01) |
| C07D 471/04 | (2006.01) |

(52) U.S. Cl.
CPC ......... *C07D 209/58* (2013.01); *C07D 235/20* (2013.01); *C07D 471/04* (2013.01); *C07F 15/0033* (2013.01); *H01L 51/508* (2013.01); *H01L 51/5064* (2013.01); *H01L 51/5278* (2013.01); *H01L 2251/55* (2013.01)

(58) Field of Classification Search
CPC ............... C07D 471/04; C07F 15/0033; H01L 2251/55; H01L 27/32; H01L 51/5064; H01L 51/508; H01L 51/5278
See application file for complete search history.

(56) References Cited

U.S. PATENT DOCUMENTS

| | | | | |
|---|---|---|---|---|
| 8,476,624 | B1* | 7/2013 | Wu | ..................... H01L 51/5004 257/40 |
| 2006/0040132 | A1 | 2/2006 | Liao et al. | |
| 2006/0087225 | A1 | 4/2006 | Liao et al. | |
| 2006/0157728 | A1 | 7/2006 | Iou | |
| 2006/0188745 | A1* | 8/2006 | Liao | ..................... H01L 51/5278 428/690 |
| 2009/0001885 | A1* | 1/2009 | Spindler | ............. H01L 51/0079 313/506 |
| 2009/0045728 | A1* | 2/2009 | Murano | .............. H01L 51/5052 313/504 |
| 2009/0304909 | A1 | 12/2009 | Daniels | |
| 2011/0248249 | A1* | 10/2011 | Forrest | ................ H01L 51/5016 257/40 |
| 2013/0228753 | A1* | 9/2013 | Moon | ................. H01L 51/5004 257/40 |
| 2015/0034923 | A1 | 2/2015 | Kim et al. | |
| 2015/0200378 | A1 | 7/2015 | Reusch et al. | |
| 2016/0248033 | A1* | 8/2016 | Uesaka | ................. H01L 51/504 |
| 2017/0213875 | A1 | 7/2017 | Bi | |

FOREIGN PATENT DOCUMENTS

| | | |
|---|---|---|
| CN | 102074658 A | 5/2011 |
| CN | 103022366 A | 4/2013 |
| CN | 103915470 A | 7/2014 |
| CN | 104183778 A | 12/2014 |
| CN | 104321896 A | 1/2015 |
| CN | 105161627 A | 12/2015 |
| CN | 105161628 A | 12/2015 |
| WO | 2014023478 A1 | 2/2014 |

OTHER PUBLICATIONS

Jul. 27, 2016—(WO) International Search Report and Written Opinion Appn PCT/CN2016/079885 with English Tran.
Oct. 1, 2018—U.S. Office Action U.S. Appl. No. 15/322,590.
Jul. 26, 2016—(WO) International Search Report and Written Opinion Appn PCT/CN2016/079884 with English Translation.
Apr. 20, 2016—(CN) First Office Action Appn 201510370289.0 with English Translation.

* cited by examiner

TANDEM ORGANIC LIGHT-EMITTING DIODE, ARRAY SUBSTRATE AND DISPLAY DEVICE

The application is a U.S. National Phase Entry of International Application No. PCT/CN2016/079885 filed on Apr. 21, 2016, designating the United States of America and claiming priority to Chinese Patent Application No. 201510370268.9 filed on Jun. 29, 2015. The present application claims priority to and the benefit of the above-identified applications and the above-identified applications are incorporated by reference herein in their entirety.

TECHNICAL FIELD

The present disclosure relates to a tandem organic light-emitting diode, an array substrate and a display device.

BACKGROUND

Currently, organic light-emitting diodes are extensively applied in display devices owing to their advantages such as low energy consumption, wide color gamut, wide viewing angle and fast response, etc. In particular, tandem organic light-emitting diodes have a low current density and can effectively avoid the thermal quenching effect caused by excess current. Therefore, tandem organic light-emitting diodes have become popular in display devices.

SUMMARY

In a first aspect, the present disclosure provides a tandem organic light-emitting diode, comprising an anode, a hole transport layer, a first light-emitting layer, a first charge generation layer, a second charge generation layer, a third charge generation layer, a fourth charge generation layer, a second light-emitting layer, an electron transport layer and a cathode which are sequentially laminated, wherein the first charge generation layer is an N-type bulk heterojunction, the second charge generation layer is a first PN junction type bulk heterojunction, the third charge generation layer is a second PN junction type bulk heterojunction, and the fourth charge generation layer is a P-type bulk heterojunction. In some embodiments, a proportion of the P-type organic material in the second charge generation layer is greater than a proportion of the N-type organic material. In some embodiments, a proportion of the P-type organic material in the third charge generation layer is less than a proportion of the N-type organic material.

In a second aspect, the present disclosure further provides an array substrate comprising a plurality of tandem organic light-emitting diodes as described above.

In a third aspect, the present disclosure further provides a display device comprising the array substrate as described above.

BRIEF DESCRIPTION OF THE DRAWINGS

In order to clearly illustrate the technical solutions of the embodiments of the present disclosure, the drawings of the embodiments are briefly described below. Apparently, the drawings described below relate to only some embodiments of the present disclosure and thus are not limitative of the present disclosure.

REFERENCE SIGNS

Figure 1:
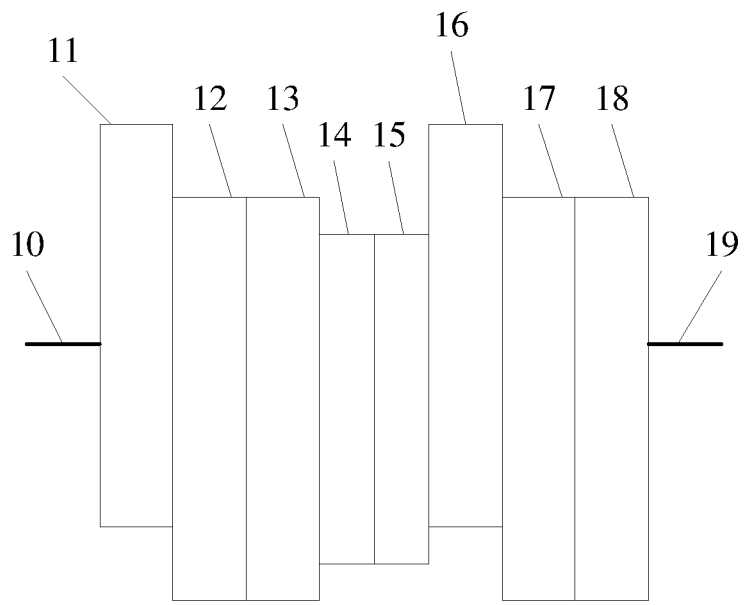
FIG. 1 is a schematic view of a tandem organic light-emitting diode according to an embodiment of the present disclosure.

10—anode,
11—hole transport layer,
12—first light-emitting layer,
13—first charge generation layer,
14—second charge generation layer,
15—third charge generation layer,
16—fourth charge generation layer,
17—second light-emitting layer,
18—electron transport layer,
19—cathode,
20—exciton-forming interface.

DETAILED DESCRIPTION

To make clearer the objects, technical solutions and advantages of the embodiments of the present disclosure, a clear and full description of the technical solutions of the embodiments of the present disclosure will be made with reference to the accompanying drawings of the embodiments of the present disclosure. Apparently, the described embodiments are just part rather than all of the embodiments of the present disclosure. Based on the embodiments of the present disclosure described, all the other embodiments obtained by a person of ordinary skill in the art, without any creative labor, fall within the scope of protection of the present disclosure.

A tandem organic light-emitting diode comprises an anode, a first hole transport layer, a first light-emitting layer, a first electron transport layer, a charge generation layer, a second hole transport layer, a second light-emitting layer, a second electron transport layer and a cathode which are laminated. In this tandem organic light-emitting diode, some carriers are provided by a driving voltage and the other carriers are generated in a charge generation layer. However, the injection efficiency of the carriers needs to be improved to ensure the luminous efficiency of the tandem organic light-emitting diode, and thus a high driving voltage is required for normal luminescence of the tandem organic light-emitting diode, which would result in high energy consumption. The tandem organic light-emitting diode has a driving voltage of about 6 V and a power efficiency of about 5.3 lm/W.

One object of the present disclosure is to provide a tandem organic light-emitting diode, an array substrate and a display device for solving the problem of high energy consumption caused by a high driving voltage required for normal luminescence of the tandem organic light-emitting diodes.

To achieve the above object, the present disclosure provides the following technical solution:

In a first aspect, the present disclosure provides a tandem organic light-emitting diode comprising an anode, a hole transport layer, a first light-emitting layer, a first charge generation layer, a second charge generation layer, a third charge generation layer, a fourth charge generation layer, a second light-emitting layer, an electron transport layer and a cathode which are sequentially laminated, wherein the first charge generation layer is an N-type bulk heterojunction; the second charge generation layer is a first PN junction type bulk heterojunction; the third charge generation layer is a second PN junction type bulk heterojunction; and the fourth charge generation layer is a P-type bulk heterojunction. In some embodiments, a proportion of the P-type organic material in the second charge generation layer is greater than a proportion of the N-type organic material. In some embodiments, a proportion of the P-type organic material in the third charge generation layer is less than a proportion of the N-type organic material.

In a second aspect, the present disclosure further provides an array substrate comprising a plurality of tandem organic light-emitting diodes as described in the above technical solution.

In a third aspect, the present disclosure further provides a display device comprising the array substrate as described in the above technical solution.

In a tandem organic light-emitting diode, a array substrate and a display device provided in the present disclosure, the first charge generation layer is an N-type bulk heterojunction, the second charge generation layer and the third charge generation layer are both PN junction type bulk heterojunctions, the fourth charge generation layer is a P-type bulk heterojunction, a proportion of the P-type organic material in the second charge generation layer is greater than a proportion of the N-type organic material, and a proportion of the P-type organic material in the third charge generation layer is less than a proportion of the N-type organic material. Therefore, an exciton-forming interface is formed respectively between the first charge generation layer and the second charge generation layer, between the second charge generation layer and the third charge generation layer, and between the third charge generation layer and the fourth charge generation layer. The above three exciton-forming interfaces are capable of generating excitons, and the number of excitons generated is increased in comparison with other tandem organic light-emitting diodes having one charge generation layer. Moreover, the carriers in the excitons do not bind to each other, and thus the number of carriers is increased, which enables a low driving voltage to ensure the injection efficiency of the carriers for normal luminescence of the tandem organic light-emitting diode, thereby reducing the power consumption for normal luminescence of the tandem organic light-emitting diode.

In order to further illustrate the tandem organic light-emitting diodes, the array substrates and the display devices provided in the embodiments of the present disclosure, the following description will be made in detail with reference to the accompanying drawings.

Figure 2:
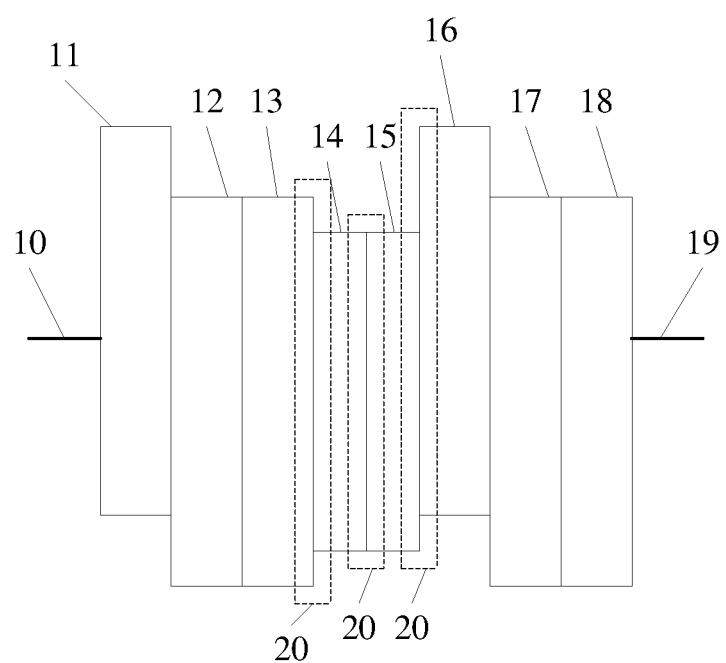
FIG. 2 is a schematic view of an exciton-forming interface in a tandem organic light-emitting diode according to an embodiment of the present disclosure.

Referring to FIG. 1, a tandem organic light-emitting diode provided in an embodiment of the present disclosure comprises an anode 10, a hole transport layer 11, a first light-emitting layer 12, a first charge generation layer 13, a second charge generation layer 14, a third charge generation layer 15, a fourth charge generation layer 16, a second light-emitting layer 17, an electron transport layer 18, and a cathode 19 which are sequentially laminated, wherein the first charge generation layer 13 is an N-type bulk heterojunction, the second charge generation layer 14 is a first PN junction type bulk heterojunction wherein a proportion of the P-type organic material in the second charge generation layer 14 is greater than a proportion of the N-type organic material, the third charge generation layer 15 is a second PN junction type bulk heterojunction wherein a proportion of the P-type organic material in the third charge generation layer 15 is less than a proportion of the N-type organic material, and the fourth charge generation layer 16 is a P-type bulk heterojunction. As shown in FIG. 2, excitons are generated in the first charge generation layer 13, the second charge generation layer 14, the third charge generation layer 15, and the fourth charge generation layer 16. An exciton-forming interface 20 is formed respectively between the first charge generation layer 13 and the second charge generation layer 14, between the second charge generation layer 14 and the third charge generation layer 15, and between the third charge generation layer 15 and the fourth charge generation layer 16. Excitons are also generated in the above three exciton-forming interfaces 20. It should be noted that the excitons generated in the first charge generation layer 13, the second charge generation layer 14, the third charge generation layer 15, the fourth charge generation layer 16 and the above three exciton-forming interfaces 20 are composed of electrons and holes, but the electrons and the holes in the excitons are not bound, i.e., the excitons in the first charge generation layer 13, the second charge generation layer 14, the third charge generation layer 15, the fourth charge generation layer 16 and the above three exciton-forming interfaces 20 provide carriers for the light-emitting layer.

In addition, as compared with other tandem organic light-emitting diodes, the tandem organic light-emitting diodes in the embodiments of the present disclosure also emit an electron transport layer for the first light-emitting layer and a hole transport layer for the second light-emitting layer, thereby reducing the injection barrier of the carriers in the tandem organic light-emitting diode. Therefore, in some embodiments, there is no electron transport layer or hole transport layer between the first light-emitting layer and the second light-emitting layer.

In a tandem organic light-emitting diode provided in an embodiment of the present disclosure, the first charge generation layer 13 is an N-type bulk heterojunction, the second charge generation layer 14 is a first PN junction type bulk heterojunction, the third charge generation layer 15 is a second PN junction type bulk heterojunction, the fourth charge generation layer 16 is a P-type bulk heterojunction, a proportion of the P-type organic material in the second charge generation layer 14 is greater than a proportion of the N-type organic material, and a proportion of the P-type organic material in the third charge generation layer 15 is less than a proportion of the N-type organic material. Therefore, an exciton-forming interface 20 is formed respectively between the first charge generation layer 13 and the second charge generation layer 14, between the second charge generation layer 14 and the third charge generation layer 15, and between the third charge generation layer 15 and the fourth charge generation layer 16. The above three exciton-forming interfaces 20 are capable of generating excitons, and the number of excitons generated is increased in comparison with other tandem organic light-emitting diodes having one charge generation layer. Moreover, the carriers in the excitons do not bind to each other, and thus the number of carriers is increased, which enables a low driving voltage to ensure the injection efficiency of the carriers for normal luminescence of the tandem organic light-emitting diode, thereby reducing the power consumption for normal luminescence of the tandem organic light-emitting diode.

In order to further ensure that the three exciton-forming interfaces 20 in the above embodiments are capable of generating excitons, the first charge generation layer 13 comprises a mixture of a first organic material and a second organic material (for example, the first charge generation layer 13 is formed from a mixture of a first organic material and a second organic material), wherein a proportion of the first organic material in the first charge generation layer 13 is greater than a proportion of the second organic material in the first charge generation layer 13, and the type of the first organic material and the type of the second organic material are not limited herein; the first organic material in the first charge generation layer 13 has an electron mobility of greater than $1\times10^{-7}$ cm$^2$/V·s, a highest occupied orbital energy level of less than −5.5 EV, and a lowest unoccupied orbital energy level of greater than −3.5 eV. The second charge generation layer 14 and the third charge generation layer 15 each independently comprise a mixture of a second organic material and a third organic material (for example, the second charge generation layer 14 and the third second charge generation layer 15 are each independently formed from a mixture of a second organic material and a third organic material), wherein the second organic material comprises an N-type organic material and has an electron mobility of greater than $1\times10^{-7}$ cm$^2$/V·s, and the third organic material comprises a P-type organic material and has a hole mobility of is greater than $1\times10^{-7}$ cm$^2$/V·s. The fourth charge generation layer 16 comprises a mixture of a third organic material and a fourth organic material (for example, the fourth charge generation layer 16 is formed from a mixture of a third organic material and a fourth organic material), wherein a proportion of the third organic material in the fourth charge generation layer 16 is less than a proportion of the fourth organic material in the fourth charge generation layer 16, and the fourth organic material in the fourth charge generation layer 16 has a hole mobility of greater than $1\times10^{-7}$ cm$^2$/V·s, a highest occupied orbital energy level of less than −5.0 eV, and a lowest unoccupied orbital energy level of greater than −3.0 eV. In addition, the first light-emitting layer 12 and the second light-emitting layer 17 each independently comprise a mixture of at least one host organic material and at least one guest organic material (for example, the first light-emitting layer 12 and the second light-emitting layer 17 each independently are formed from a mixture of at least one host organic material and at least one guest organic material).

The specific organic materials constituting the first charge generation layer 13, the second charge generation layer 14, the third charge generation layer 15 and the fourth charge generation layer 16 will be described below with specific examples. For example, the first organic material is TPBi (i.e., 1,3,5-tris(1-phenyl-1H-benzimidazole-2-yl)benzene), the second organic material is C$_{60}$, and the third organic material is rubrene, pentacene, tetrafluorotetracyanoquinonedimethane, or a phthalocyanine derivative, wherein a proportion of the third organic material in the second charge generation layer 14 is greater than a proportion of the second organic material in the second charge generation layer 14 while a proportion of the third organic material in the third charge generation layer 15 is less than a proportion of the second organic material in the third charge generation layer 15; and the fourth material is TCTA (i.e., 4,4',4"-tri(carbazol-9-yl) triphenylamine).

Alternatively, the first organic material is Bphen (i.e., 4,7-diphenyl-1,10-phenanthroline) and the second organic material is C$_{60}$; the second charge generation layer 14 and the third charge generation layer 15 are both formed by mixing the second organic material with a third organic material, wherein the third organic material is rubrene, pentacene, tetrafluorotetracyanoquinonedimethane, or a phthalocyanine derivative, a proportion of the third organic material in the second charge generation layer 14 is greater than a proportion of the second organic material in the second charge generation layer 14 while a proportion of the third organic material in the third charge generation layer 15 is less than a proportion of the second organic material in the third charge generation layer 15; and the fourth organic material is TAPC (i.e., 1,1-bis[4-[N,N-di(p-tolyl)amino]phenyl]cyclohexane).

For a more detailed description of the particular composition of the tandem organic light-emitting diode in the embodiments of the present disclosure, specific organic materials of the first charge generation layer 13, the second charge generation layer 14, the third charge generation layer 15 and the fourth charge generation layer 16, as well as the specific organic materials constituting other layers of the tandem organic light-emitting diode will be exemplified below.

EMBODIMENT

Embodiment 1

Taking a tandem organic light-emitting diode which emitted blue light as an example, the anode 10 of the tandem organic light-emitting diode was a bottom emitting glass substrate with indium tin oxide and had a thickness of 100 nm; the hole transport layer 11 was a TCTA layer and had a thickness of 90 nm; in the first light-emitting layer 12, the host organic material comprised TCTA and TPBi, wherein TCTA had a hole mobility of $1\times10^{-3}$ cm$^2$/V·s, a highest occupied orbital energy level of −5.7 eV, a lowest unoccupied orbital energy level of −2.6 eV, and a triplet energy level of 2.76 eV, and TPBi had an electron mobility of $8.0\times10^{-4}$ cm$^2$/V·s, a highest occupied orbital energy level of −6.2 eV, a lowest unoccupied orbital energy level of −2.7 eV, and a triplet energy level of 2.6 eV; and the guest organic material was Flrpic (i.e., bis[2-(4,6-difluorophenyl)pyridinato-C$^2$,N](picolinato)iridium(III)) having a triplet energy level of 2.62 eV. The triplet energy levels of the two host organic materials were both greater than that of the guest organic material, such that energy transfer could be better achieved between the host and guest organic materials of the light-emitting layer. The first light-emitting layer 12 had a thickness of 20 nm; the first charge generation layer 13 was formed by mixing TPBi with C$_{60}$ and had a thickness of 50 nm, wherein C$_{60}$ had an electron mobility of 0.1 cm$^2$/V·s, a highest occupied orbital energy level of −6.2 eV, and a lowest unoccupied orbital energy level of −4.6 eV; the second charge generation layer 14 was formed by mixing C$_{60}$ with rubrene, wherein a proportion of rubrene in the second charge generation layer 14 was greater than a proportion of C$_{60}$ in the second charge generation layer 14, the second charge generation layer 14 had a thickness of 10 nm, and rubrene had a hole mobility of 0.1 cm$^2$/V·s, a highest occupied orbital energy level of −5.36 eV, and a lowest unoccupied orbital energy level of −3.1 eV; the third charge generation layer 15 was formed by mixing C$_{60}$ with rubrene, wherein a proportion of rubrene in the third charge generation layer 15 was less than a proportion of C$_{60}$ in the third charge generation layer 15 and the third charge generation layer 15 had a thickness of 10 nm; the fourth charge generation layer 16 was formed by mixing TCTA with rubrene and had a thickness of 50 nm; the second light-emitting layer 17 had the same specific materials as the first light-emitting layer 12, and had a thickness of 20 nm; the electron transport layer 18 was a TmPyPb (i.e., 1,3,5-tris[(3-pyridyl)-3-phenyl]benzene) layer and had a thickness of 30 nm; and the cathode 19 was a magnesium-silver alloy layer and had a thickness of 120 nm.

Embodiment 2

Still taking a tandem organic light-emitting diode which emitted blue light as an example, the hole transport layer 11 was a TAPC layer; in the first light-emitting layer 12, the host organic material comprised TAPC and Bphen, wherein TAPC had a highest occupied orbital energy level of −5.4 eV and a lowest unoccupied orbital energy level of −2.4 eV, and Bphen had an electron mobility of $4.2\times10^{-4}$ cm$^2$/V·s, a highest occupied orbital energy level of −6.1 eV and a lowest unoccupied orbital energy level of −2.8 eV, and the guest organic material was FIrpic; the first charge generation layer 13 was formed by mixing Bphen with $C_{60}$; the second charge generation layer 14 was formed by mixing $C_{60}$ with rubrene, wherein a proportion of rubrene in the second charge generation layer 14 was greater than a proportion of $C_{60}$ in the second charge generation layer 14; the third charge generation layer 15 was formed by mixing $C_{60}$ with rubrene, wherein a proportion of rubrene in the third charge generation layer 15 was less than a proportion of $C_{60}$ in the third charge generation layer 15; the fourth charge generation layer 16 was formed by mixing TAPC with rubrene; the second light-emitting layer 17 had the same specific materials as the first light-emitting layer 12; and the electron transport layer 18 was a Bphen layer.

The above tandem organic light-emitting diode which emitted blue light had a luminous main peak located at 472 nm and a shoulder peak located at 496 nm. The tandem organic light-emitting diodes in Embodiments 1 and 2 had a driving voltage of 5.5 V and 5.0 V and a power efficiency of 6.4 lm/W and 7.0 lm/W, respectively.

The production process of the above tandem organic light-emitting diodes which emitted blue light will be described below. Firstly, a bottom emitting glass substrate (i.e., anode 10) with indium tin oxide was cleansed in an ultrasonic environment of deionized water, acetone, and anhydrous ethanol sequentially followed by drying the bottom emitting glass substrate with indium tin oxide using $N_2$, plasma cleansing to remove oxides, placing the bottom emitting glass substrate with indium tin oxide in a vapor deposition chamber with a vacuum degree of less than $5\times10^{-4}$ Pa, and subjecting the bottom emitting glass substrate with indium tin oxide to vacuum vapor deposition to deposit a hole transport layer 11, a first light-emitting layer 12, a first charge generation layer 13, a second charge generation layer 14, a third charge generation layer 15, a fourth charge generation layer 16, a second light-emitting layer 17, an electron transport layer 18, and a cathode 19 sequentially on the bottom emitting glass substrate with indium tin oxide. A metal cathode mask was used in the vapor deposition process of the cathode 19 at an evaporation rate of 0.3 nm/s; and an open mask was used in the vapor deposition process of the other layers at an evaporation rate of 0.1 nm/s.

It should be noted that the above embodiments merely describe the specific materials of the tandem organic light-emitting diode which emits blue light, but replacement or variation of the specific materials of the tandem organic light-emitting diode which emits other color lights is also encompassed within the scope of protection of the present disclosure.

Embodiments of the present disclosure further provide an array substrate comprising a plurality of tandem organic light-emitting diodes according to the above embodiments. The tandem organic light-emitting diodes in the array substrate have the same advantages as the tandem organic light-emitting diodes in the above embodiments, and thus no further detail will be provided here.

Embodiments of the present disclosure further provide a display device comprising an array substrate according to the above embodiments. The array substrate in the display device has the same advantages as the array substrate in the above embodiments, and thus no further detail will be provided here.

In the description of the above embodiments, particular features, structures, materials, or characteristics may be combined in any one or more embodiments or examples in a suitable manner.

The above are merely exemplary embodiments of the present disclosure, and are not intended to limit the scope of protection of the present disclosure, which is yet determined by the appended claims.

The present application claims the priority of the Chinese patent application No. 201510370268.9 submitted on Jun. 29, 2015, and the content disclosed in the above Chinese patent application is incorporated herein by reference as part of the present application.

The invention claimed is:

1. A tandem organic light-emitting diode comprising an anode, a hole transport layer, a first light-emitting layer, a first charge generation layer, a second charge generation layer, a third charge generation layer, a fourth charge generation layer, a second light-emitting layer, an electron transport layer, and a cathode which are sequentially laminated,
    wherein the first charge generation layer is an N-type bulk heterojunction, the second charge generation layer is a first PN junction type bulk heterojunction, the third charge generation layer is a second PN junction type bulk heterojunction, and the fourth charge generation layer is a P-type bulk heterojunction;
    the first charge generation layer comprises a mixture of a first organic material and a second organic material;
    the second charge generation layer and the third charge generation layer each independently comprise a mixture of the second organic material and a third organic material, the second organic material comprising an N-type organic material, the third organic material comprising a P-type organic material;
    a proportion of the P-type organic material in the second charge generation layer is greater than that of the N-type organic material; and
    a proportion of the P-type organic material in the third charge generation layer is less than that of the N-type organic material.

2. The tandem organic light-emitting diode according to claim 1, wherein a proportion of the first organic material in the first charge generation layer is greater than a proportion of the second organic material in the first charge generation layer, and the first organic material has an electron mobility of greater than $1\times10^{-7}$ cm$^2$/V·s, a highest occupied orbital energy level of less than −5.5 eV and a lowest unoccupied orbital energy level of greater than −3.5 eV.

3. The tandem organic light-emitting diode according to claim 2, wherein the second organic material having an electron mobility of greater than $1\times10^{-7}$ cm$^2$/V·s and the third organic material having a hole mobility of greater than $1\times10^{-7}$ cm$^2$/V·s.

4. The tandem organic light-emitting diode according to claim 3, wherein the fourth charge generation layer comprises a mixture of the third organic material and a fourth organic material, a proportion of the third organic material in the fourth charge generation layer is less than a proportion of the fourth organic material in the fourth charge generation layer, and the fourth organic material has a hole mobility of greater than $1\times10^{-7}$ cm$^2$/V·s, a highest occupied orbital energy level of less than −5.0 eV and a lowest unoccupied orbital energy level of greater than −3.0 eV.

5. The tandem organic light-emitting diode according to claim 4, wherein the first organic material comprises 1,3,5-tris(1-phenyl-1H-benzimidazole-2-yl)benzene; the second organic material comprises $C_{60}$; the third organic material comprises at least one selected from the group consisting of rubrene, pentacene, tetrafluorotetracyanoquinodimethane, or a phthalocyanine derivative; and the fourth organic material comprises 4,4',4"-tri(carbazol-9-yl) triphenylamine.

6. The tandem organic light-emitting diode according to claim 4, wherein the first organic material comprises 4,7-diphenyl-1,10-phenanthroline; the second organic material comprises $C_{60}$; the third organic material comprises at least one selected from the group consisting of rubrene, pentacene, tetrafluorotetracyanoquinodimethane, or a phthalocyanine derivative; and the fourth organic material comprises 1,1-bis[4-[N,N-di(p-tolyl)amino]phenyl]cyclohexane.

7. The tandem organic light-emitting diode according to claim 1, wherein the first light-emitting layer and the second light-emitting layer each independently comprise a mixture of at least one host organic material and at least one guest organic material.

8. The tandem organic light-emitting diode according to claim 7, wherein the guest organic material comprises bis[2-(4,6-difluorophenyl)pyridinato-$C^2$,N](picolinato) iridium(III); the host organic material comprises 4,4',4"-tri (carbazol-9-yl)triphenylamine and 1,3,5-tris(1-phenyl-1H-benzimidazole-2-yl)benzene, or the host organic material comprises 1,1-bis[4-[N,N-bis(p-tolyl)amino]phenyl]cyclohexane and 4,7-diphenyl-1,10-phenanthroline.

9. An array substrate, comprising a plurality of tandem organic light-emitting diodes according to claim 1.

10. A display device, comprising the array substrate according to claim 9.

11. The array substrate according to claim 9, wherein a proportion of the first organic material in the first charge generation layer is greater than a proportion of the second organic material in the first charge generation layer, and the first organic material has an electron mobility of greater than $1\times10^{-7}$ $cm^2/V\cdot s$, a highest occupied orbital energy level of less than −5.5 eV and a lowest unoccupied orbital energy level of greater than −3.5 eV.

12. The array substrate according to claim 11, wherein the second organic material having an electron mobility of greater than $1\times10^{-7}$ $cm^2/V\cdot s$ and the third organic material having a hole mobility of greater than $1\times10^{-7}$ $cm^2/V\cdot s$.

13. The array substrate according to claim 12, wherein the fourth charge generation layer comprises a mixture of the third organic material and a fourth organic material, a proportion of the third organic material in the fourth charge generation layer is less than a proportion of the fourth organic material in the fourth charge generation layer, and the fourth organic material has a hole mobility of greater than $1\times10^{-7}$ $cm^2/V\cdot s$, a highest occupied orbital energy level of less than −5.0 eV and a lowest unoccupied orbital energy level of greater than −3.0 eV.

14. The array substrate according to claim 13, wherein the first organic material comprises 1,3,5-tris(1-phenyl-1H-benzimidazole-2-yl)benzene; the second organic material comprises $C_{60}$; the third organic material comprises at least one selected from the group consisting of rubrene, pentacene, tetrafluorotetracyanoquinodimethane, or a phthalocyanine derivative; and the fourth organic material comprises 4,4',4"-tri(carbazol-9-yl) triphenylamine.

15. The array substrate according to claim 13, wherein the first organic material comprises 4,7-diphenyl-1,10-phenanthroline; the second organic material comprises $C_{60}$; the third organic material comprises at least one selected from the group consisting of rubrene, pentacene, tetrafluorotetracyanoquinodimethane, or a phthalocyanine derivative; and the fourth organic material comprises 1,1-bis[4-[N,N-di(p-tolyl)amino]phenyl]cyclohexane.

16. The array substrate according to claim 9, wherein the first light-emitting layer and the second light-emitting layer each independently comprise a mixture of at least one host organic material and at least one guest organic material.

17. The array substrate according to claim 16, wherein the guest organic material comprises bis[2-(4,6-difluorophenyl) pyridinato-$C^2$,N](picolinato)iridium(III); the host organic material comprises 4,4',4"-tri(carbazol-9-yl)triphenylamine and 1,3,5-tris(1-phenyl-1H-benzimidazole-2-yl)benzene, or the host organic material comprises 1,1-bis[4-[N,N-bis(p-tolyl)amino]phenyl]cyclohexane and 4,7-diphenyl-1,10-phenanthroline.

* * * * *